(12) United States Patent
Abe (10) Patent No.: US 9,395,406 B2
(45) Date of Patent: Jul. 19, 2016

(54) INSPECTION METHOD FOR SEMICONDUCTOR LIGHT-EMITTING DEVICE AND MANUFACTURING METHOD FOR SEMICONDUCTOR LIGHT-EMITTING DEVICE

(71) Applicant: NICHIA CORPORATION, Anan-shi (JP)

(72) Inventor: Masatoshi Abe, Anan (JP)

(73) Assignee: NICHIA CORPORATION, Anan-Shi (JP)

( * ) Notice: Subject to any disclaimer, the term of this patent is extended or adjusted under 35 U.S.C. 154(b) by 144 days.

(21) Appl. No.: 14/168,953

(22) Filed: Jan. 30, 2014

(65) Prior Publication Data

US 2014/0210995 A1 Jul. 31, 2014

(30) Foreign Application Priority Data

Jan. 31, 2013 (JP) .................. 2013-017586

(51) Int. Cl.
 *G01R 31/26* (2014.01)
 *G01N 21/64* (2006.01)
 *H01L 33/00* (2010.01)
 *G01R 31/265* (2006.01)

(52) U.S. Cl.
 CPC ........ *G01R 31/2635* (2013.01); *G01N 21/6489* (2013.01); *H01L 33/005* (2013.01); *G01R 31/2656* (2013.01)

(58) Field of Classification Search
 CPC ........... G01N 21/6489; G01R 31/2635; G01R 31/2656; H01L 33/005
 USPC .................................................. 382/141, 152
 See application file for complete search history.

(56) References Cited

U.S. PATENT DOCUMENTS

| 2009/0136120 A1 | 5/2009 | Onushkin et al. |
| 2009/0296090 A1* | 12/2009 | Saha .................. G01N 21/9501 356/369 |
| 2013/0211736 A1* | 8/2013 | Hess .......................... G03F 1/84 702/34 |
| 2013/0250095 A1* | 9/2013 | Inoue .................... G06T 7/0004 348/94 |

FOREIGN PATENT DOCUMENTS

| JP | 63-250835 A | 10/1988 |
| JP | 2004-170374 A | 6/2004 |
| JP | 2006-266780 A | 10/2006 |
| JP | 2009-128366 A | 6/2009 |

* cited by examiner

*Primary Examiner* — Edward Park
(74) *Attorney, Agent, or Firm* — Foley & Lardner LLP (57) ABSTRACT

An inspection method for a semiconductor light-emitting device includes an image capturing step for irradiating light to the semiconductor light emitting device so as to excite an active layer and capturing an image of photoluminescence released from the active layer, an inspection region extracting step for extracting an inspection region of the captured image, a luminance average determination step for, determining as defective when a luminance average is smaller than a predetermined threshold, a luminance variance determination step for determining as defective when a luminance variance is larger than a predetermined threshold, and a total determination step for totally determining the semiconductor light-emitting device as defective when determined the semiconductor light emitting device as defective in at least one of the two determination results.

20 Claims, 5 Drawing Sheets

Fig.2

| SAMPLE | PHOTOLUMINESCENCE IMAGE | AVERAGE | DETERMINATION 1 | LUMINANCE DISTRIBUTION | VARIANCE | DETERMINATION 2 | TOTAL DETERMINATION |
|---|---|---|---|---|---|---|---|
| | | | DETERMINATION THRESHOLD=80 | | | DETERMINATION THRESHOLD=10 | |
| 1 |  | 140 | ○ |  255 / 0 | 0 | ○ | ○ |
| 2 |  | 60 | × |  255 / 0 | 0 | ○ | × |
| 3 |  | 100 | ○ |  255 / 0 | 100 | × | × |

INSPECTION METHOD FOR SEMICONDUCTOR LIGHT-EMITTING DEVICE AND MANUFACTURING METHOD FOR SEMICONDUCTOR LIGHT-EMITTING DEVICE

CROSS-REFERENCE TO RELATED APPLICATIONS

This application claims the benefit of Japanese patent application No. 2013-017586, filed on Jan. 31, 2013, which is incorporated by reference.

TECHNICAL FIELD

The present invention relates to an inspection method for a semiconductor light-emitting device and a manufacturing method for a semiconductor light-emitting device including the inspection method.

BACKGROUND ART

Generally, LED (Light-Emitting Diode), which are semiconductor light-emitting devices, are manufactured by stacking semiconductor layers of mutually different conductive types on a growth substrate to sandwich an active layer there between and further by forming electrodes on the semiconductor layers of the individual conductive types. Manufactured semiconductor light-emitting devices are subjected to inspections for light emitting performance and the like so that acceptable devices are selected.

As inspections for light emitting performance of semiconductor light-emitting devices in their wafer state, there have conventionally been performed appearance inspection for inspecting the presence of flaws or the like under visible light, and light emitting inspection in which light emitting is executed by providing electric currents between positive and negative pad electrodes with use of a prober. In the light emitting inspection with a prober, since the needle (probe) of the prober needs to be put into contact with the electrodes of individual semiconductor light-emitting devices, there have been involved a quite long time for inspection and a fear of flaws on the semiconductor light-emitting devices due to the contact of the probe. Moreover, with small-sized semiconductor light-emitting devices, because their pad electrodes are also small in size, there has been difficulty in properly contacting of the probe with the devices.

Therefore, as a method of inspection for light emitting performance without providing electric currents through the semiconductor light-emitting devices, there has been proposed a method that the active layer of semiconductor light-emitting devices is excited with light irradiation and photoluminescence light released from the excited active layer is observed.

For example, Japanese Unexamined Patent Application Publication No. 2009-128366 describes a light-emitting device inspection method including the steps of irradiating a semiconductor light-emitting device with ultraviolet light, capturing a light emitting image generated by a photoluminescence effect in the active layer with use of a CCD (Charge Coupled Device) camera and, based on photoluminescence intensity information therefrom, determining quality of the semiconductor light-emitting device.

Figure 2:
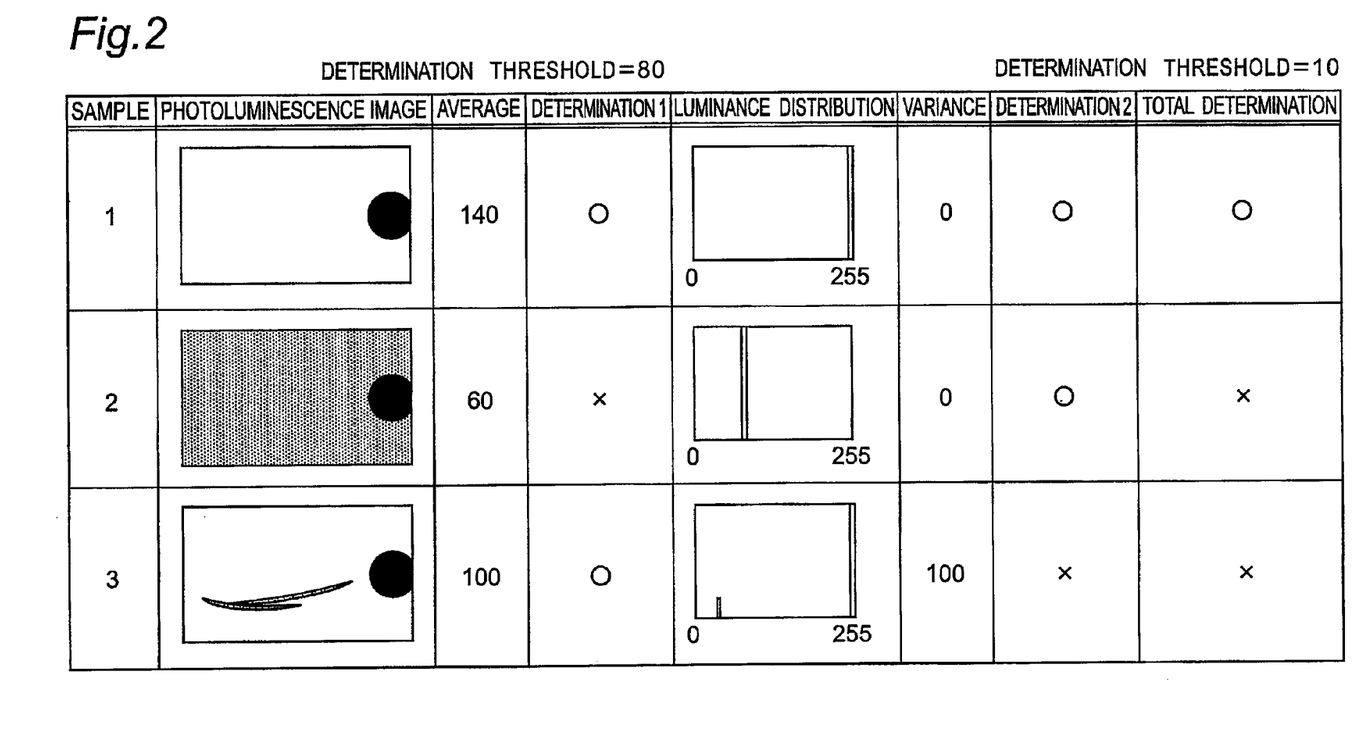
FIG. 2 is an explanatory view for explaining an outline of the semiconductor light-emitting device inspection method according to the first embodiment of the invention.

Referring now to FIG. 2, the method for determining quality of the light-emitting devices by using the photoluminescence intensity released from the active layer is explained. FIG. 2 is an explanatory view for explaining an outline of the light-emitting device inspection method. Also, shown in the field of image of photoluminescence in FIG. 2 are images obtained by capturing an aspect that the active layer of the light-emitting device excited by light irradiation releases photoluminescence.

In the image of photoluminescence of each sample, a black circular region on the right edge side is a non-emitting region where the p-type semiconductor layer and the active layer are eliminated for formation of the n-type electrode so that the region structurally does not emit light.

In the case where the quality of a light-emitting device in semiconductor light-emitting devices is determined based on photoluminescence intensity information as in the inspection method described in Japanese Unexamined Patent Application Publication No. 2009-128366, it is common practice to determine that each semiconductor light-emitting device is determined as acceptable on condition that light released from the semiconductor light-emitting device is equal to or higher than a predetermined intensity.

In the case where the entire surface except the non-emitting region emits light with sufficient intensity as in the case of sample 1, the semiconductor light-emitting device is determined as an acceptable device. In the case where the entire surface emits light with insufficient intensity as in sample 2, the semiconductor light-emitting device is determined as a defective device.

CITATION LIST

Patent Literature

Patent literature 1. Japanese Unexamined Patent Application Publication No. 2009-128366

SUMMARY OF INVENTION

However, in a determination method using average luminance, even if a light-emitting device partly includes a light-emitting defective region of no light emitting or considerably lower luminance level than other light-emitting regions due to defects such as internal flaws caused during manufacture as in the case of sample 3 shown in FIG. 2, the light-emitting device, which emits light at a predetermined intensity or higher as one light-emitting device, i.e. which has an average luminance of a predetermined value or higher, is determined as acceptable. Light-emitting devices having such defective light-emitting regions as shown above should basically be rejected as defective devices because those light-emitting devices, even if capable of light emitting at a predetermined intensity or higher immediately after their manufacture, are likely to decline in intensity, moreover highly likely to fail, due to time deterioration.

In the case where such defects causing defective light-emitting as shown above appear externally, the defects can be detected by conventional appearance inspections. However, for example, in the case where defects occur to the internal active layer the defects could not be detected by appearance inspections.

The present invention, having been accomplished in view of these and other problems, has an object of providing a semiconductor light-emitting device inspection method for properly detecting defective devices through analysis of images of photoluminescence released from semiconductor light-emitting devices excited by light irradiation, and a semiconductor light-emitting device manufacturing method including this inspection method as a process.

In order to solve the above-described problems, a semiconductor light-emitting device inspection method according to the present invention is an inspection method for a semiconductor light-emitting device having an active layer, comprising: an image input step for irradiating light of a shorter wavelength than light emitted from the active layer to the semiconductor light-emitting device and inputting a captured image of photoluminescence emitted from the active layer; an inspection region extracting step for extracting, a region of the semiconductor light-emitting device based on the captured image, as an inspection region; a photoluminescence intensity average determination step for calculating an average value of the photoluminescence intensity over the pixels in the inspection region and determining the semiconductor light-emitting device as defective when the average value is smaller than a predetermined first threshold; and a photoluminescence intensity variation determination step for calculating a variation value indicating a degree of variation of the photoluminescence intensity over the pixels in the inspection region and determining the semiconductor light-emitting device as defective when the variation value is larger than a predetermined second threshold, wherein upon obtaining defective determination in at least one of the photoluminescence intensity average determination step and the photoluminescence intensity variation determination step, determine the semiconductor light-emitting device is defective.

Also, a semiconductor light-emitting device manufacturing method according to the invention comprises: a semiconductor light-emitting device formation step for forming a semiconductor light-emitting device; an inspection step for inspecting the semiconductor light-emitting device formed in the semiconductor light-emitting device formation step to determine whether or not the semiconductor light-emitting device is defective; and a screening step for screening the semiconductor light-emitting device as acceptable when the semiconductor light-emitting device is not determined as defective in the inspection step, wherein the inspection step is implemented by the inspection method for a semiconductor light-emitting device as described above.

According to the inspection method for a semiconductor light-emitting device of the invention, since semiconductor light-emitting devices of large photoluminescence intensity variation in addition to semiconductor light-emitting devices of low an average the photoluminescence intensity determined as defective, defective device can properly be detected.

Also, according to the semiconductor light-emitting device manufacturing method of the invention, since semiconductor light-emitting devices are screened based on a determining quality by the above-described inspection method, defective devices can properly be excluded.

DESCRIPTION OF EMBODIMENTS

Hereinbelow, inspection methods for a semiconductor light-emitting device and manufacturing methods for a semiconductor light-emitting device according to embodiments of the present invention will be described in detail with reference to the accompanying drawings. It is to be noted here that the accompanying drawings referenced in the following description schematically show the invention, so that scales, intervals, positional relations and the like among individual members may be exaggerated or part of those members may be omitted in depiction. Also in the following description, the same designations and reference signs denote the same or equivalent members in principle with their detailed description omitted as appropriate.

First Embodiment (Principle of Inspection Method)

Referring first to FIG. 2, the principle of the inspection method for a semiconductor light-emitting device (hereinafter, referred to as "inspection method" as appropriate) according to a first embodiment of the invention will be described.

FIG. 2 shows an example in which images of photoluminescence are schematically shown for explanation of the principle of the inspection method.

The inspection method according to the first embodiment of the invention is intended to determine whether or not a semiconductor light-emitting device (hereinafter, referred to as light-emitting device as appropriate), which is an inspection object, is acceptable or defective through the steps of irradiating the light-emitting device with light for excitation of the active layer, and analyzing an image of photoluminescence obtained by capturing an image of photoluminescence released from the excited active layer.

More specifically, in the inspection method according to this embodiment, in addition to a mean photoluminescence intensity emitted from a light-emitting region, the presence of any light-emitting defective region formed in the light-emitting region is detected, and when a light-emitting defective region is detected, the light-emitting device is determined as defective even though the average photoluminescence intensity is equal to or higher than a predetermined value. The detection of a light-emitting defective region is performed based on the degree indicating variation of photoluminescence intensity (e.g., variance or standard deviation) in the light-emitting region. That is, the presence of any light-emitting defective region is determined by utilizing the property that the variation of photoluminescence intensity within the light emitting device increases in the case where a light emitting defective region of very low photoluminescence intensity exists.

In samples 1-3 shown in FIG. 2, as described above, images of photoluminescence are shown with luminance used as the index indicating the photoluminescence intensity. In this case, it is assumed each luminance is expressed in 256-step pixel values where the luminance of the darkest portion is '0' and the luminance of the brightest portion is '255.'

The average photoluminescence of a light-emitting region, which is an inspection region of each sample, is as shown in the 'average' field of FIG. 2. Assuming that a determination threshold for determining quality of the semiconductor light-emitting device based on an average photoluminescence is '80,' samples 1 and 3 are determined as acceptable devices and sample 2 is determined as a defective device, as marked by ○ (acceptable device) and X (defective device) in the field of 'Determination 1.'

As described above, even in the case where light-emitting regions include a defective light-emitting region due to an internal defective or the like as in sample 3, when luminance of the other regions are high and the average value among all the light-emitting regions is equal to or higher than the determination threshold, the light-emitting device cannot be detected as a defective device.

Meanwhile, histograms showing pixel luminance distributions of pixels of the light-emitting regions in these samples are shown in a field of 'luminance distribution.' These histograms schematically show relative frequencies against the frequency of the most frequent luminance on the assumption that the horizontal axis represents the luminance and the vertical axis represents the frequency.

Sample 1 show that all the pixels emit light at the highest luminance. Therefore, there are no luminance differences among pixels, where the variance, which is the index of variation in photoluminescence intensity, is '0.'

In sample 2, although the luminance is low, yet there are no luminance differences among pixels, where the variance is '0.'

In sample 3, the light-emitting regions include light-emitting defective regions that do no emit light at all or that are considerably lower in luminance level than the other light-emitting regions, where the luminance distributions are bipolarized into the highest luminance and the lowest luminance. Thus, the variance is as large as '100.'

In this case, given that the determination threshold based on the luminance variance is '10,' samples 1, 2 are determined as acceptable devices and sample 3 is determined as a defective device, as marked by ○ (acceptable device) and X (defective device) in the field of 'Determination 2.'

In the case described above, the terms "light-emitting defective regions that are considerably lower in luminance level than the other light-emitting regions" refer to being of lower level than the range of luminance unevenness permitted as acceptable devices. Also, the examples of the determination threshold by luminance average, the determination threshold by luminance variance, luminance distribution and the like shown in FIG. 2 are schematic exemplifications for explaining the principle of the inspection method and these are not limited.

In the inspection method according to this embodiment, the determination of the quality is made by considering both of a determination result based on the luminance average and a determination result based on the luminance variance. That is, on condition that a light-emitting device is determined as defective in at least one of the two determinations, the light-emitting device is determined as defective. In other words, on condition that a light-emitting device is determined as defective in neither of the two determinations (i.e. determined as acceptable in both determinations), the light-emitting device is determined as acceptable.

Accordingly, in the case shown in FIG. 2, sample 1 is totally determined as acceptable and samples 2 and 3 are totally determined as defective, as marked by ○ (acceptable device) and X (defective device) in the field of 'Total determination.'

In addition, for evaluation of the variance, pixels that structurally become non-emitting regions are excluded. Those pixels that become non-emitting regions, normally having a luminance of '0' or a very low value, show a pixel value equivalent to those of light-emitting defective regions due to flaws or the like. For this reason, including pixels of non-emitting regions to calculate a variance would make it impossible to distinguish the calculated variance from variances resulting when defective light-emitting regions are included.

Thus, in the inspection method of the invention, variances are calculated excluding pixels that structurally become non-emitting regions beforehand. In addition, when no non-emitting regions are involved structurally, pixel values of the entire region of the light-emitting device may be used to calculate the variance.

Also, for calculation of the luminance average, even without excluding pixels of non-emitting regions, lessening the determination threshold in consideration of decreases in the luminance average due to non-emitting regions makes it possible to determine quality of the semiconductor light-emitting device on the same basis as in the case where the non-emitting regions are excluded. However, it is preferable that also for the determinations based on the luminance average, the luminance average is calculated with pixels of non-emitting regions excluded, in which case the luminance average value is increased so that the determination precision is improved.

It is noted that the determination threshold for luminance average as well as the determination threshold for luminance variance as described above are exemplifications for explaining the principle of the inspection method, and these are not limited. These determination thresholds may appropriately be predetermined by empirically determining distributions of luminance averages and luminance variances in acceptable-device samples as well as distributions of luminance averages and luminance variances in defective-device samples so that acceptable devices and defective devices can properly be determined.

In this embodiment, the quality determination based on the luminance average is made by using only the lower-limit threshold. However, the determination using the upper-limit threshold may be further performed. Among light-emitting devices having flaws or other defects, in spite of their being defective devices, there are some cases where photoluminescence is observed apparently at luminances higher than those of acceptable light-emitting devices because photoluminescence propagating from adjacent light-emitting devices is diffracted or scattered in the light-extraction plane direction by the defective portions. In the case of such defective light-emitting devices, quality determination can properly be achieved by setting an upper-limit threshold and determining the light-emitting device as defective also when the luminance average is larger than the upper-limit threshold.

In the case where the upper-limit threshold is provided, gain of an image capturing means 22 is adjusted so that the pixel value corresponding to the highest luminance observed in acceptable light-emitting devices becomes lower than the highest value of the pixel values of an image capturing means 22. With the pixel value given by 8-bit data, the pixel value corresponding to the highest luminance of acceptable-device light-emitting devices is set to '150' as an example. Then, with the upper-limit threshold set to '150,' light-emitting devices having a luminance average over '150,' i.e. exceeding the highest value of luminance average of acceptable light-emitting devices may appropriately be determined as defective.

(Configuration of Inspection Apparatus)

Next, the configuration of an inspection apparatus for performing the inspection method according to the first embodiment of the invention will be described with reference to FIG. 1.

Figure 1:
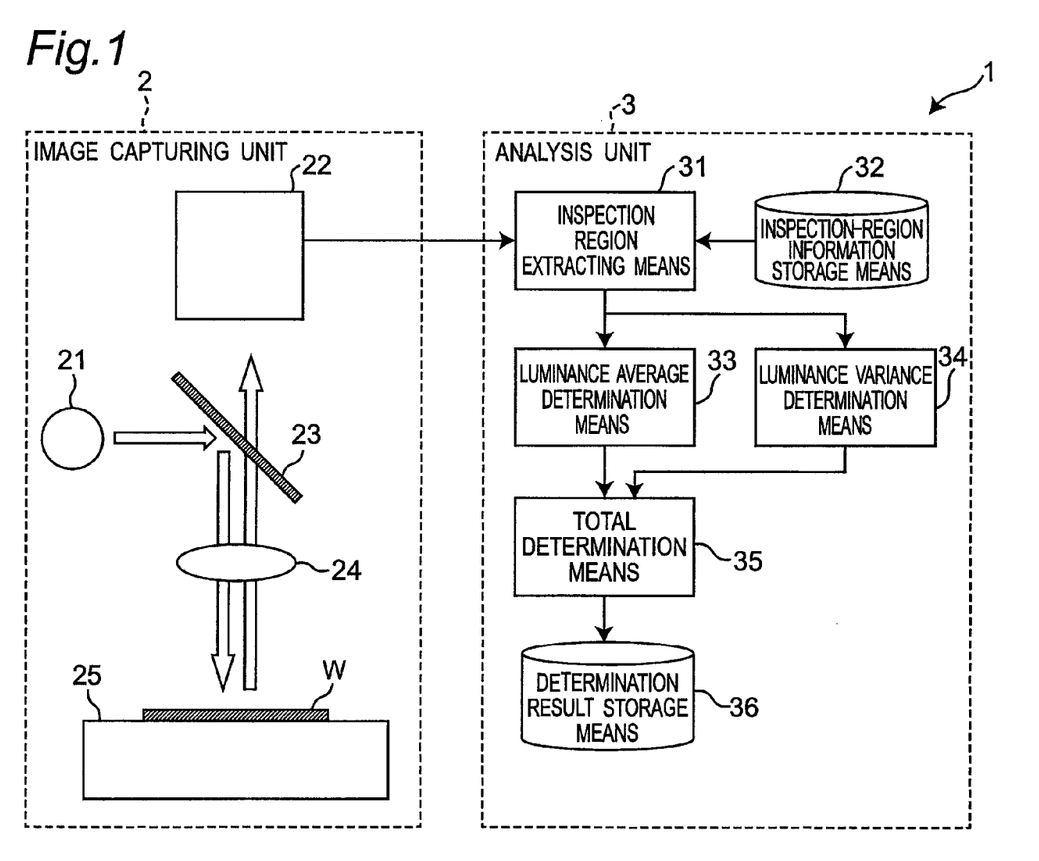
FIG. 1 is a view showing a configuration of an inspection apparatus for executing a semiconductor light-emitting device inspection method according to a first embodiment of the present invention.

As shown in FIG. 1, the inspection apparatus 1 of this embodiment is composed of an image capturing unit 2 and an analysis unit 3.

The image capturing unit (image input means) 2 is to capture an image of photoluminescence released from the active layer by irradiation of light-emitting devices with excitation light. For this purpose, the image capturing unit 2 in this embodiment includes an irradiating light source 21, an image capturing means 22, a dichroic mirror 23, an objective lens 24, and a mount 25.

In this embodiment, an inspection object W is assumed as a wafer-state one in which light-emitting devices are formed in two-dimensional array in the following description, but this is not limited. For example, the inspection object W may be a single light-emitting device or may be light-emitting devices divided into chips from a wafer division and re-arrayed on a support substrate or the like. Furthermore, the inspection object W may be light-emitting devices obtained by bonding a support substrate on the opposite side surface to a growth substrate of wafer-state light-emitting devices and further peeling the growth substrate off so that the light-emitting devices are transferred to the support substrate.

The irradiating light source 21 is a light source for generating light of wavelength that can excite the active layer of the light-emitting device constituting the inspection object W. The excitation light needs only to include light of shorter wavelength than wavelength of the light emitted from the active layer of the light-emitting device to be inspected. For example, for light-emitting devices that emit green light, blue or purple light can be used as the excitation light. For light-emitting devices that emit blue light, visible light of shorter wavelength than the blue light can be used as the excitation light.

As such an irradiating light source 21 is LED, laser diode, xenon arc lamp, mercury arc lamp, and the like can be used.

In the case where semiconductor layers other than the active layer of light-emitting device emits photoluminescence light by the photoluminescence effect, it is preferable that light of a wavelength range capable of selectively exciting the active layer is used as the excitation light. For example, with gallium nitride-based semiconductor used as the semiconductor material of light-emitting devices, GaN is excited by near-ultraviolet light to emit yellow photoluminescence. Therefore, it is preferable to use excitation light of a wavelength range capable of selectively exciting the active layer without including near-ultraviolet light. As a result, the quality of light emitting by the active layer of light-emitting devices can be inspected properly.

Also, in the case where the light source itself has a wide emitting wavelength range, the irradiating light source 21 may also be constituted by combining optical filters and spectroscopes as required so as to generate excitation light for selectively exciting the active layer.

The image capturing means 22 is an image capturing device such as a CCD image sensor and a CMOS (complementary metal oxide semiconductor) image sensor to capture image of photoluminescence of the inspection object W. The image capturing means 22 outputs data of captured image of photoluminescence to the analysis unit.

For the image capturing means 22, a monochrome image sensor which has sensitivity to wavelength of photoluminescence from the inspection object W can be used. Also, the image capturing means 22 can be employed to a color image sensor. In a case where a color image sensor is used, captured images of photoluminescence can be obtained and can be separated into three colors of R (Red), G (Green) and B (Blue), as example. Also, In the case where a color image sensor is used, although image data of a color component that is the most sensitive to the wavelength of the photoluminescence is preferably used, yet data resulting from weighting to those color components on the pixel basis may also be used.

The dichroic mirror 23, which is a reflection member having wavelength selectivity of reflected light, reflects light of a particular wavelength range derived from the irradiating light source 21 as excitation light toward the inspection object W side and moreover transmits photoluminescence derived from the inspection object W toward the image capturing means 22 side.

In addition, the dichroic mirror 23 can have such characteristics as to reflect excitation light of desired wavelength according to the inspection object W.

In a case where the light from the irradiating light source 21 is only that of wavelength effective as excitation light, a half mirror can also be used instead of the dichroic mirror 23.

The objective lens 24 is a lens for converging excitation light coming from the irradiating light source 21 via the dichroic mirror 23 to an image capturing region of the inspection object W and for forming an image of photoluminescence from the inspection object W on an image capturing surface of the image capturing means 22.

In this embodiment, the dichroic mirror 23 is provided between the image capturing means 22 and the objective lens 24. However, without being limited to this, a camera in which an image capturing device and an objective lens are integrally included may also be used.

The mount 25 is for placing and holding thereon the inspection object W. In this embodiment, the mount 25 is formed by using an XY stage which is movable in two directions on a horizontal plane. By driving the XY stage to move the inspection object W within the horizontal plane, an image-capturing range of one-time capture by the image capturing means 22 can be changed as required. Thus, images of the inspection object W can be captured in a plurality of divided regions.

The analysis unit 3 is for analyzing an image of photoluminescence of the inspection object W inputted from the image capturing unit 2 to determine quality of individual light emitting devices constituting the inspection object W is acceptable or not. For this purpose, the analysis unit 3 in this embodiment includes an inspection region extracting means 31, an inspection-region information storage means 32, a luminance average determination means 33, a luminance variance determination means 34, a total determination means 35, and a determination result storage means 36.

The inspection region extracting means 31 receives an input of an image of photoluminescence of the inspection object W from the image capturing means 22 of the image capturing unit 2 and the image of photoluminescence divides into image regions on the light-emitting device basis. Further, with respect to each of the divided image regions on the one light-emitting device basis, extracts only image data of inspection regions as inspection region images, one after another, by referencing inspection-region information which is information for discriminating between inspection regions being inspection objects and non-inspection regions being excluded out of inspection objects in the relevant light-emitting device previously stored in the inspection-region information storage means 32. The inspection region extracting means 31 outputs extracted inspection region images on the light-emitting device basis to the luminance average determination means 33 and the luminance variance determination means 34.

Details of the inspection region and the non-inspection region in a light-emitting device will be described later.

The inspection-region information storage means 32 stores inspection-region information that is information for discriminating between inspection regions, which are taken as objects of the inspection, and non-inspection regions, which are not taken as objects of the inspection, in the light-emitting device which is to be inspected. Herein, the term 'inspection regions' refers to the region (light-emitting region) of a light emitting device which includes an active layer and released photoluminescence in a plan view (in the plane to be captured) of the light-emitting device. Also, the term 'non-inspection region' refers to a region where no light is emitted due to structural reasons of the light emitting device (non-emitting region) for example, having no active layer so that an n-side electrode is formed. Inspection-region information stored in the inspection-region information storage means 32 is referenced by the inspection region extracting means 31.

In this case, it is assumed that the inspection-region information is previously stored (registered) in the inspection-region information storage means 32 prior to the inspection. Instead of being previously registered as in this embodiment, the inspection-region information may also be inputted to the inspection region extracting means 31, as required, from external, e.g. via communication lines, depending on the type of inspection objects.

The luminance average determination means (photoluminescence intensity average determination means) 33 receives inputs of inspection region images from the inspection region extracting means 31 on the light-emitting device basis to calculate a luminance average, which is an average of luminance values (photoluminescence intensity) among inspection region images on the light-emitting device basis. Then, the luminance average determination means 33 compares a luminance average threshold (first threshold), which is a predetermined determination threshold, and the calculated luminance average with each other so as to determine the light-emitting device as defective when the luminance average is smaller than the luminance average threshold and to determine the light-emitting device as acceptable when the luminance average is equal to or larger than the luminance average threshold. The luminance average determination means 33 outputs the determination to the total determination means 35.

In this embodiment, the luminance value is used to indicate the degree of the photoluminescence intensity, but it is not limited thereto and other indices may also be used if they show the photoluminescence intensity. For example, the index may be the luminance value corresponding to the Y value in the CIE (Commission Internationale de l' Eclairage) 1931 standard colorimetric system, or may be the value calculated by weighting RGB-separated color image data with proper weighting (e.g., 0.3:0.6:0.1) applied to R, G and B in accordance with the relative luminous sensitivity, or may be the pixel value for any one of the color components having the highest sensitivity to the wavelength of photoluminescence.

The luminance variance determination means (photoluminescence intensity variation determination means) 34 receives inputs of inspection region images from the inspection region extracting means 31 on the light-emitting device basis and calculates a luminance variance that is a variance (variation) of luminance values (photoluminescence intensity) in inspection region images on the light-emitting device basis. Then, the luminance variance determination means 34 compares a luminance variance threshold (second threshold), which is a predetermined determination threshold, and a calculated luminance variance with each other so as to determine the light-emitting device as defective when the luminance variance is larger than the luminance variance threshold and to determine the light-emitting device as acceptable when the luminance variance is equal to or smaller than the luminance variance threshold. The luminance variance determination means 34 inputs the determination to the total determination means 35.

In this embodiment, the luminance variance is used to indicate the degree of a variation of the photoluminescence intensity, but it is not limited thereto. As to photoluminescence intensity other indices which indicate photoluminescence intensity may also be used as in the foregoing case of the luminance average determination means 33. Also as a degree of the variation, the standard deviation shown Equation (2) or the average deviation shown in Equation (3) can be used instead of the variance shown in Equation (1), and moreover the coefficient of variation (CV) obtained by dividing the standard deviation by the average as shown in Equation (4) can be used.

$$\text{variance} = \Sigma(Xi - X\text{ave})^2/N \qquad \text{Eq. (1)}$$

$$\text{standard deviation} = \sqrt{(\text{variance})} \qquad \text{Eq. (2)}$$

$$\text{average deviation} = \Sigma |Xi - X\text{ave}|/N \qquad \text{Eq. (3)}$$

$$\text{coefficient of variation} = (\text{standard deviation})/(\text{average}). \qquad \text{Eq. (4)}$$

In the above equations, Xi represents the luminance of the i-th pixel, Xave represents the luminance average of all the pixels of an inspection region, N represents the number of pixels in the inspection region, and $\Sigma$ represents a sum of the right side terms for all the pixels of the inspection region.

The total determination means 35 receives inputs of determination results on the light-emitting device basis from the luminance average determination means 33 and the luminance variance determination means 34, respectively, so as to totally determine the quality of the light-emitting device from the determination results of both determination means. The total determination means 35 in this embodiment determines the light-emitting device as acceptable when neither of the two determination results is defective, and determines the light-emitting device as defective when at least one of the two determination results is defective. The total determination means 35 stores the determination results in the determination result storage means 36 corresponding to the light-emitting devices.

The determination result storage means 36 stores determination results obtained by the total determination means 35 in association with light-emitting devices. Determination results stored in the determination result storage means 36 are used for, for example, screening manufactured light-emitting devices.

In this embodiment, the total determination means 35 is so designed as to make a total determination by using determination results obtained by the luminance average determination means 33 and the luminance variance determination means 34 and to store total determination results in the determination result storage means 36, but it is not limited. For example, determination results derived from the luminance average determination means 33 and determination results derived from the luminance variance determination means 34 may be stored in the determination result storage means 36 in association with light-emitting devices, instead of total determination results or in addition to total determination results. Also, in the case where screening light-emitting devices is performed immediately after the determination by using determination results, the screening of light-emitting devices may be performed by using those determination results without storing the determination results in the determination result storage means 36.

It is also allowable that determination by the luminance average determination means 33 and determination by the luminance variance determination means 34 are executed one by one and, in response to each of the two determination results, defective devices are excluded one by one. As a result of this, when a determination as defective made in any one of the two determination results, the light-emitting device can be excluded. That is, without performing the total determination, a screening equivalent to the screening of light-emitting devices based on the total determination result can be achieved. Also, in the case where the two determinations are performed one by one, when a first determination result is defective, the other determination may be omitted because the relevant light-emitting device results as defective even when the total determination is performed.

In this embodiment, predetermined fixed values are used as the determination threshold by luminance average and the determination threshold by luminance variance, but it is not limited. In consideration of fluctuations in the state of capturing image and interlot variation, the determination thresholds may be corrected as appropriate.

For example, it is also allowable that with respect to a plurality of light-emitting devices captured in a one-screen image by the image capturing unit 2, a luminance average of all the light-emitting devices is first calculated and then the determination threshold is corrected depending on the average degree of the luminance average.

As a result, the quality determination can be performed more properly by correcting light quantity variations of the light source 21 of the image capturing unit 2 over time and luminance deviations among inspection-object lots.

For this purpose, luminance averages are empirically determined previously for samples of a multiplicity (e.g., several hundreds to thousands) of light-emitting devices, and further an average of luminance average of all samples is calculated and stored in storage means as a standard luminance average (reference luminance average) of light-emitting devices. Also, a luminance-average determination threshold and a luminance-variance determination threshold for properly inspecting the inspection object W comprised of a group of light-emitting devices that emit light at the standard luminance average level are previously determined as reference values (luminance-average reference determination threshold and luminance-variance reference determination threshold).

Then, in the inspection of the inspection object W, first, an average among luminance averages of light-emitting devices (inspection-object luminance average) captured in a one-screen image by the image capturing unit 2 is calculated. In this case, a value resulting from multiplying a luminance-average reference determination threshold by a ratio of the inspection-object luminance average to a reference luminance average is used as the luminance-average determination threshold of the inspection object W as shown in Equation (5). Also for luminance variance, as in the case of the luminance average, a luminance-variance determination threshold is corrected depending on the value of the inspection-object luminance average as shown in Equation (6).

$$\text{luminance-average determination threshold} = (\text{luminance-average reference determination threshold}) \times (\text{inspection-object luminance average})/(\text{reference luminance average}) \quad \text{Eq. (5)}$$

$$\text{luminance-variance determination threshold} = (\text{luminance-variance reference determination threshold}) \times (\text{inspection-object luminance average})/(\text{reference luminance average}) \quad \text{Eq. (6)}$$

Also, the correction method for determination thresholds is not limited to correcting the determination threshold proportionally to the magnitude of the inspection-object luminance average, and the determination threshold may also be corrected so as to be nonlinear to the magnitude of the inspection-object luminance average. Furthermore, the determination threshold may be corrected by adding or subtracting an offset value in accordance with the magnitude of an inspection-object luminance average to or from the reference determination threshold.

Instead of the correction of a determination threshold described above, the luminance average and the luminance variance for each light-emitting device of the inspection object W may be corrected. For example, a correction method for the luminance average and the luminance variance corresponding to the examples shown in Equations (5) and (6) is that the luminance average and the luminance variance are multiplied by a correction factor obtained by dividing reference luminance average 'by inspection-object luminance average.' Then, the quality of the light-emitting device is determined in comparison to the determination threshold which is a fixed value. As a result, a correction effect equivalent to the determination threshold correction method can be obtained.

The analysis unit 3 can also be implemented by inspection programs by which a computer containing such hardware resources as a CPU (Central Processing Unit) and storage means (e.g., memory, hard disk) is operated cooperatively as the respective means described above. These programs may be distributed via communication lines or distributed after they are written in recording mediums such as optical disc or magnetic disc and flash memory.

(Inspection Region and Non-Inspection Region)

Next, inspection region and non-inspection region in light-emitting device will be explained with reference to FIGS. 3A, 3B and 3C.

The inspection object W in this embodiment is provided in a wafer state in which light-emitting devices 10 are two-dimensionally arrayed. Therefore, a plurality of light-emitting devices 10 are shown in a captured image of photoluminescence as shown in FIG. 3A. In this embodiment, the image of photoluminescence is divided into individual light-emitting device 10, and moreover pixels of a predetermined inspection region are extracted from a divisional image of one light-emitting device 10.

(Dividing Light-Emitting Device Region)

Figure 3A:
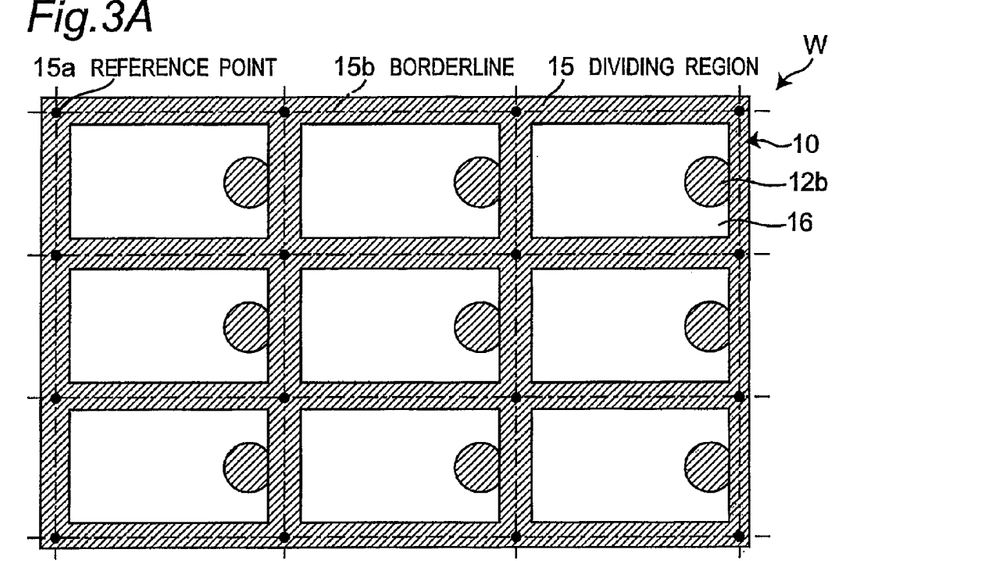
FIG. 3A is a schematic bottom view showing a structure of an inspection object in the semiconductor light-emitting device inspection method according to the first embodiment of the invention.

In the wafer-state inspection object W, as shown in FIG. 3A, a plurality of light-emitting devices 10 are two-dimensionally arrayed on one growth substrate. The individual light-emitting devices 10 are divided longitudinally and laterally by dividing regions 15. The dividing regions 15, from which semiconductor layers are eliminated, become non-emitting regions structurally. In the wafer, light-emitting devices 10 are regularly placed in predetermined shape and arrangement. Then, in the photoluminescence image, the dividing regions 15 are observed as dark longitudinal-and-lateral grid lines as shown by hatching in FIG. 3A, so that light-emitting regions 16 of the light-emitting devices 10 appear to be partitioned by the grid lines. Thus, for example, with centers of the grid lines taken as borderlines 15b, the image of photoluminescence can be divided into image regions of the individual light-emitting devices 10.

In addition, in FIG. 3A, circular-shaped regions hatched on the right-edge side of the light-emitting region 16 are region for forming an n-side electrode and region corresponding to recess portion 12b of the semiconductor layers from which the active layer is eliminated. The structure of the light-emitting devices 10 will be described later.

(Extraction of Inspection Region)

In this embodiment, only regions that structurally become light-emitting regions are taken as inspection regions and targeted for calculation of the above-described luminance average and luminance variance. Therefore, pixels that structurally become non-emitting regions are extracted as non-inspection regions and excluded from the images of the individual light-emitting devices 10 so that only pixels of light-emitting regions are extracted as inspection regions.

With the division that one region partitioned by the borderlines 15b is regarded as an image region for one light-emitting device 10 as described above, since the light-emitting devices 10 are regularly arrayed, structures of the same configuration are placed at the same positions in the image of any one light-emitting device 10, for example with a left-upper intersecting point of the borderlines 15b taken as a reference point 15a.

Figure 3B:
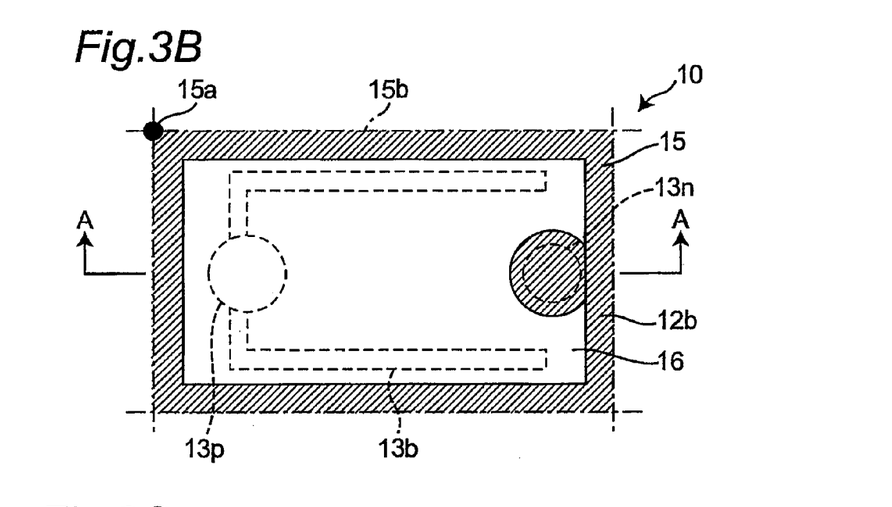
FIG. 3B is a partial enlarged view of FIG. 3A.

Referring to FIG. 3B, which shows an image of photoluminescence of one light-emitting device 10, with the reference point 15a taken as a reference, the light-emitting region 16, the dividing region 15 and the recess portion 12b as non-emitting regions (hatched regions) can be previously determined in correspondence to the structure of the light-emitting device 10. In this embodiment, with the reference point 15a taken as a reference, inspection-region information, which is map information for discriminating whether each pixel within the divisional image of one light-emitting device 10 corresponds to an inspection region or a non-inspection region, is previously prepared and stored in the inspection-region information storage means 32 (see FIG. 1). Then, this inspection-region information is referenced by the inspection region extracting means 31 (see FIG. 1) so that only pixels of inspection regions are extracted.

Figure 3C:
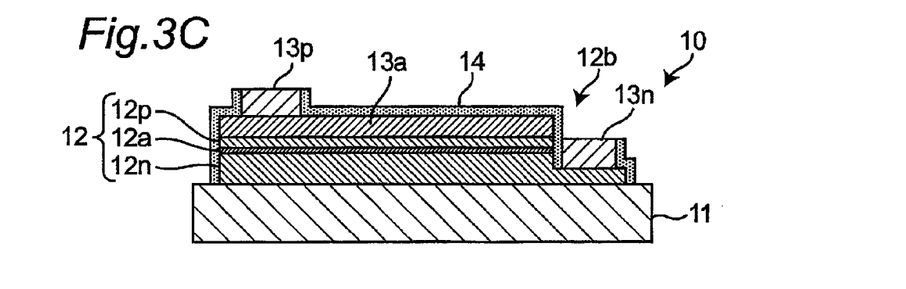
FIG. 3C is a sectional view taken along the line A-A of FIG. 3B.

Referring now to FIG. 3C, the relationship between the light-emitting regions 16, which are inspection regions, as well as the non-emitting regions, which are non-inspection regions, and the structure of the light-emitting devices 10 is explained below. The structure of the light-emitting devices 10 described in this case is only an example and not intended to limit the structure of the light-emitting devices 10, which are the object of the inspection.

For example, the size of one light-emitting device 10 as in a plan view is about 500 μm×300 μm. Alsor, the size may be either larger one or smaller one. Also, its plan-view shape is not limited to rectangular ones, and light-emitting devices 10 of any appropriate shape such as circular, elliptical and polygonal shapes are applicable. Furthermore, number and shape of the non-emitting regions are also not limited.

The light-emitting device 10 shown in FIG. 3C is composed of a light-pervious growth substrate 11, a semiconductor multilayered body 12 having an n-type semiconductor layer 12n, an active layer 12a and a p-type semiconductor layer 12p multilayered therein, a p-side electrode 13p and an n-side electrode 13n which are positive and negative pad electrodes, respectively, a reflective diffusion electrode 13a for diffusing an electric current from the p-side electrode 13p to the almost all surface of the p-type semiconductor layer 12p, and a light-pervious protective film 14. The semiconductor multilayered body 12 has a recess portion 12b formed at a right-end portion where the entire p-type semiconductor layer 12p and the entire active layer 12a and part of the n-type semiconductor layer 12n have been removed from the top surface to the downward direction. The n-side electrode 13n is provided at the bottom of the recess portion 12b so as to be in electrical contact with the n-type semiconductor layer 12n.

Also, the p-side electrode 13p is provided so as to be in electrical contact with the p-type semiconductor layer 12p via the diffusion electrode 13a. In the dividing regions 15, which are outer-edge regions of the light-emitting devices 10, the semiconductor multilayered body 12 is removed.

In addition, the n-side electrode 13n, the p-side electrode 13p and the diffusion electrode 13a are formed of metal layers as an example, being assumed as light-impervious.

In this example, the diffusion electrode 13a is a reflecting electrode, and this light-emitting device 10 is a face-down mounting type device having a light-extracting surface on its growth substrate 11 side. Therefore, image of the photoluminescence is captured from the growth substrate 11 side. In this case, the recess portion 12b, is a non-emitting region because it has no active layer 12a. As viewed from the growth substrate 11 side, the recess portion 12b and the dividing region 15 become non-emitting regions while the rest of the region is the light-emitting region, i.e., inspection region.

In addition, in the case where the diffusion electrode 13a is a light-pervious electrode and the light-emitting device 10 is a face-up mounting type device, the image of photoluminescence may be captured from the side on which the semiconductor multilayered body 12 is provided. In this case, as shown by broken line in FIG. 3B, a region shielded from light by the p-side electrode 13p is added to the non-inspection region as a non-emitting region in addition to the dividing region 15 and the recess portion 12b, which are original non-emitting regions. Further, in the case where an extensive portion 13b formed of a metal layer is provided to improve the current diffusivity from the p-side electrode 13p to the diffusion electrode 13a, the region where the extensive portion 13b shown by broken line in FIG. 3B is provided is also added to the non-inspection region.

Even in the case of the face-up mounting type device, when the image is captured from the light-pervious growth substrate 11 side, neither the p-side electrode 13p nor the stretched portion 13b makes a shield from photoluminescence, making it unnecessary to add these regions to non-inspection regions.

As shown above, the inspection regions can be determined depending on the structure of the light-emitting device 10 and the direction of image capturing.

In addition, in order that all the regions having the active layer 12a are inspected for the presence of any light-emitting defective region, it is preferable to capture the image in a direction in which there are no such shielding matters as the p-side electrode 13p or the stretched portion 13b as described above.

(Operations of Inspection Apparatus)

Next, operations of the inspection apparatus 1 will be explained with reference to FIG. 4 (reference to FIG. 1 as required).

Figure 4:
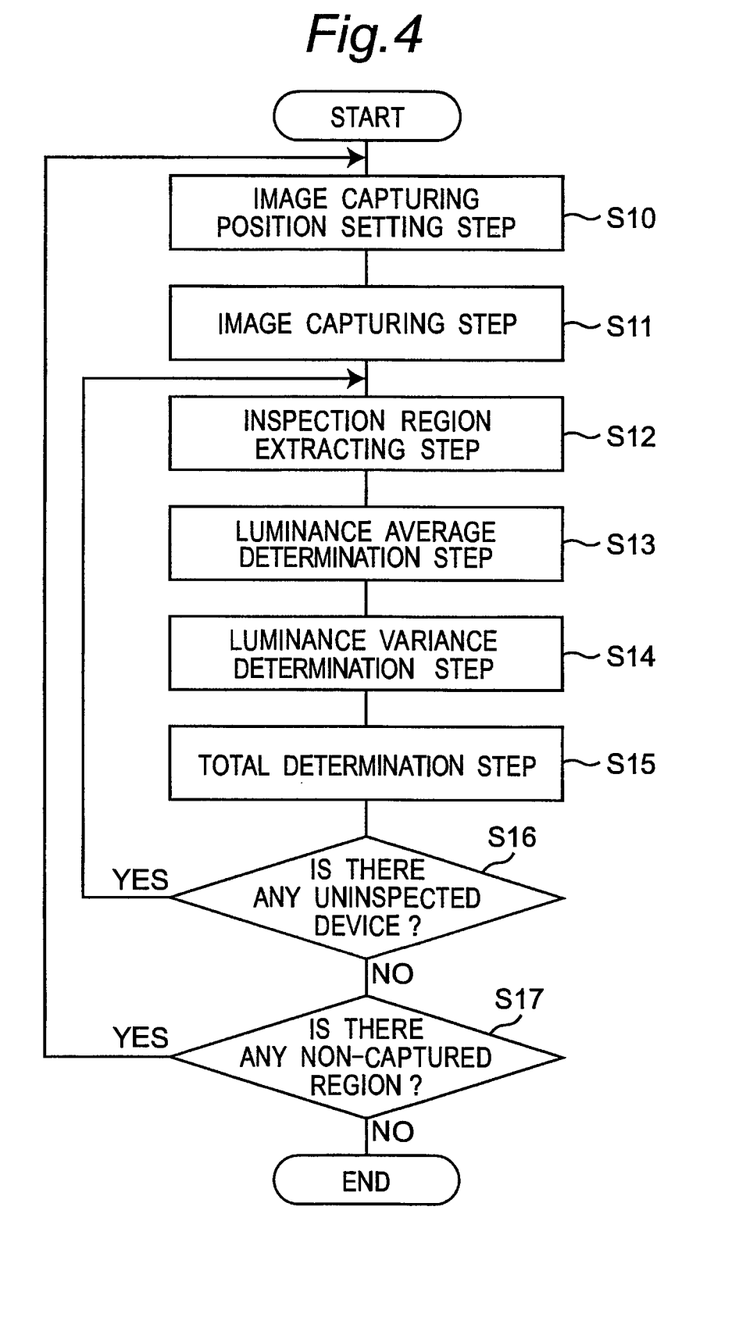
FIG. 4 is a flowchart showing the flow of the semiconductor light-emitting device inspection method according to the first embodiment of the invention.

In this embodiment, as shown in FIG. 4, the inspection apparatus 1 performs an image capturing position setting step S10, an image capturing step S11, an inspection region extracting step S12, a luminance average determination step S13, a luminance variance determination step S14, and a total determination step S15 for all the regions of the wafer, which is the inspection object W, on the light-emitting device 10 basis.

First, at the image capturing position setting step S10, as the inspection object W is mounted on the mount 25 of the image capturing unit 2, the inspection apparatus 1 drives the mount 25, which is an XY stage, so as to set an image capturing position in the inspection object W.

Next, at the image capturing step (image input step) S11, the inspection apparatus 1 capturing a photoluminescence image of the inspection object W by the image capturing unit 2. More specifically, the inspection apparatus 1 turns on the irradiating light source 21 to irradiate the inspection object W with irradiating light via the dichroic mirror 23 and the objective lens 24 for exciting the inspection object W. As a result of this, photoluminescence is released from the inspection object W excited by the irradiating light, and the released photoluminescence is inputted to the image capturing means 22 via the objective lens 24 and further through the dichroic mirror 23. Then, the inspection apparatus 1 generates photoluminescence image data, which is obtained by converting incident photoluminescence into photoluminescence intensity signals on the pixel basis, by the image capturing means 22.

Next, at the inspection region extracting step S12, the inspection apparatus 1 divides the captured image of photoluminescence at step S11 into images on the one light-emitting device 10 basis by the inspection region extracting means 31. On this occasion, the inspection apparatus 1 extracts image data of pixels in the inspection region from the divided image by referencing the inspection-region information stored in the inspection-region information storage means 32.

Next, at the luminance average determination step (photoluminescence intensity average determination step) S13, the inspection apparatus 1 calculates, by the luminance average determination means 33, a luminance average, which is an average of pixel values showing luminance, as to image data of the inspection region extracted at step S12. Then, the inspection apparatus 1 compares, by the luminance average determination means 33, the calculated luminance average with a predetermined determination threshold for use in determination based on luminance averages. On this occasion, the light-emitting device is determined as acceptable when the luminance average is equal to or larger than the determination threshold. When the light-emitting device is determined as defective when the luminance average is smaller than the determination threshold.

Next, at the luminance variance determination step (photoluminescence intensity variation determination step) S14, the inspection apparatus 1 calculates, by the luminance variance determination means 34, a luminance variance, which is a variance of pixel value showing luminance, as to image data of the inspection region extracted at step S12. Then, the inspection apparatus 1 compares, by the luminance variance determination means 34, the calculated luminance variance with a predetermined determination threshold for use in determination based on luminance variances. On this occasion, the light-emitting device is determined as acceptable when the luminance variance is equal to or smaller than the determination threshold. When the light-emitting device is determined as defective when the luminance variance is larger than the determination threshold.

Either of the process of step S13 or the process of step S14 may be performed first. Moreover the two processes may be performed in parallel.

Next, at the total determination step S15, the inspection apparatus 1 references, by the total determination means 35, the result determined at step S13 and the result determined at step S14, where the light-emitting device 10 is determined as defective when at least one of the two results is a determination as a defective device. The result of this total determination is stored in the determination result storage means 36 in association with the inspection-object light-emitting device 10.

Next, the inspection apparatus 1 checks, by the analysis unit 3, whether or not there remains any image of uninspected light-emitting devices 10 in the image of photoluminescence captured at step S11 (step S16). When there remains any image (Yes at step S16), the processing flow returns to step S12, followed by analysis of an image of the next uninspected light-emitting device 10.

Meanwhile, when there remains no uninspected light-emitting device 10 (No at step S16), the inspection apparatus 1 checks, by the analysis unit 3, whether or not there remains any non-captured region of the inspection object W (step S17). When there remains any non-captured region (Yes at step S17), the processing flow returns to step S10, where an image capturing position is set for the image capturing of the next region by the image capturing unit 2.

On the other hand, when there remains no non-captured region (No at step S17), the inspection apparatus 1 finishes the processing.

In this embodiment, the inspection object W, in which a plurality of light-emitting devices 10 are arrayed, is divided into a plurality of regions and captured for images one by one, and images of a plurality of light-emitting devices 10 in dividing regions are separated one by one so as to be inspected. However, this is not limited. For example, it is also possible that the whole inspection object W is captured for an image by one-time image capturing. In this case, the loop determination of step S17 is unnecessary. It is also allowable that one light-emitting device 10 is captured in one image. In this case, the loop determination of step S16 is unnecessary. Furthermore, it is allowable that the inspection object W is a single light-emitting device 10. In this case, the loop determinations of step S16 and step S17 are unnecessary.

Second Embodiment (Manufacturing Method of Semiconductor Light-Emitting Device)

Next, as a second embodiment of the invention, a semiconductor light-emitting device manufacturing method including the inspection method according to the first embodiment as an inspection step will be described below with reference to FIG. 5 (also reference to FIGS. 1, 3A, 3B and 3C as required).

In this embodiment, the light-emitting device 10 having structure shown in FIG. 3C is explained as an example of the semiconductor light-emitting device to be manufactured. Also, nitride semiconductor is explained as an example of the semiconductor material, as follows.

Figure 5:
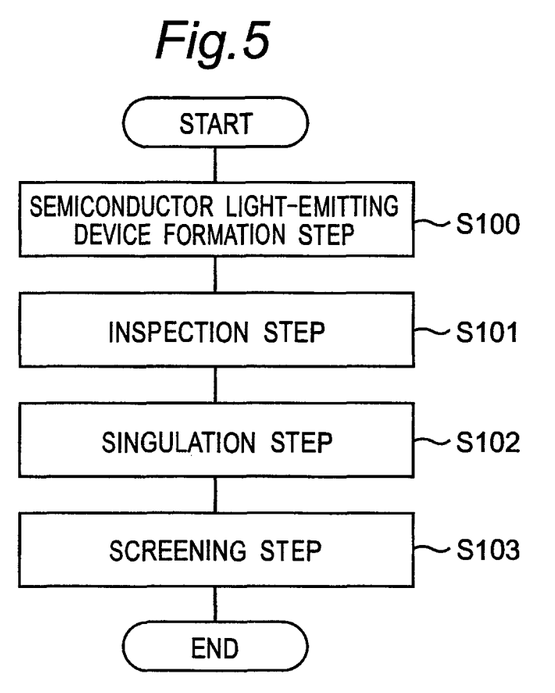
FIG. 5 is a flowchart showing the flow of a semiconductor light-emitting device manufacturing method according to a second embodiment of the invention.

As shown in FIG. 5, the semiconductor light-emitting device manufacturing method according to the second embodiment includes a semiconductor light-emitting device formation step S100, an inspection step S101, a singulation step S102, and a screening step S103. These steps are performed in succession.

(Semiconductor Light-Emitting Device Formation Step)

At the semiconductor light-emitting device formation step S100, semiconductor light-emitting devices 10 having structure as shown in FIG. 3C are formed in a wafer state of two-dimensional array.

In more detail, first, a semiconductor multilayered body 12 in which an n-type semiconductor layer $12n$, an active layer $12a$ and a p-type semiconductor layer $12p$ are laminated successively is formed on a growth substrate 11 formed from sapphire or the like.

Specific compositions of the n-type semiconductor layer $12n$, the active layer $12a$ and the p-type semiconductor layer $12p$ are not particularly limited, and materials suitable for semiconductor light-emitting devices such as GaN, GaAs, InGaN, AlInGaP, GaP, SiC and ZnO may be used. In particular, GaN-based compound semiconductors represented by a general formula of $In_XAl_YGa_{1-X-Y}N$ ($0 \leq X$, $0 \leq Y$, $X+Y \leq 1$) can preferably be used as nitride semiconductor materials.

Each of these semiconductor layers may have a single-layer structure but may have a multilayer structure which contains layers different in composition, film thickness or the like from one another a superlattice structure or the like. In particular, the active layer 12a is preferably provided in a single quantum well structure or multiple quantum well structure formed of multilayered thin films having the quantum effect.

Generally, such semiconductor layers may be made up in a homostructure, heterostructure or double-heterostructure or the like having MIS junction, PIN junction or PN junction. GaN-based compound semiconductor layers can be formed by known techniques such as MOCVD (Metal Organic Chemical Vapor Deposition), HVPE (Hydride Vapor Phase Epitaxy), MBE (Molecular Beam Epitaxy), or other processes. Also, film thicknesses of the semiconductor layers are not particularly limited, and those of various film thicknesses are applicable.

The multilayer structure of the semiconductor layers may be exemplified by a buffer layer made of AlGaN, an undoped GaN layer, an n-side contact layer made of Si-doped n-type GaN, a superlattice layer in which a GaN layer and an InGaN layer are alternately stacked, an active layer of the multiquantum well structure in which a GaN layer and an InGaN layer are alternately stacked, a superlattice layer in which a Mg-doped AlGaN layer and a Mg-doped InGaN layer are alternately stacked, a p-side contact layer made of Mg-doped GaN, and the like.

With the semiconductor multilayered body 12 formed in the way shown above, in a region of part of the top surface of the semiconductor multilayered body 12, a recess portion 12b in which the n-type semiconductor layer 12n is exposed at the bottom surface is formed by removing part of the p-type semiconductor layer 12p, the active layer 12a and the n-type semiconductor layer 12n by etching process.

Concurrently with this the semiconductor multilayered body 12 of the dividing regions 15 for partitioning the individual light-emitting devices 10, is also removed by etching process. In addition, with regard to the dividing regions 15, part of the n-type semiconductor layer 12n may be removed as in the recess portion 12b, or the entirety of the n-type semiconductor layer 12n may be removed so as to make the growth substrate 11 exposed.

Next, an n-side electrode 13n, which is a pad electrode, is formed on the bottom surface of the recess portion 12b. Also, in regions that become light-emitting regions where neither the p-type semiconductor layer 12p nor the active layer 12a is removed, a p-side electrode 13p, which is a pad electrode, is formed at part of the diffusion electrode 13a, as well as its top surface, that covers substantially entire surface of the top surface of the p-type semiconductor layer 12p.

Further, on the whole surface of the wafer, an insulative protective film 14 of $SiO_2$ or the like is formed, for example, by sputtering.

By the above-described processes, the semiconductor light-emitting devices 10 in the wafer state are formed.

(Inspection Step)

Next, at the inspection step S101, the quality of the light emitting property is determined on the basis of each semiconductor light-emitting device 10 formed in the wafer. The quality inspection step S101 is performed by the inspection method according to the first embodiment described above. Therefore, description of the inspection step S101 is omitted.

In addition, quality determination results which are inspection results, are stored in the determination result storage means 36 in association with the individual semiconductor light-emitting devices 10.

(Singulation Step)

Next, at the singulation step S102, the wafer is divided according to the dividing regions 15 by dicing process, scribing process or the like so as to divide the wafer into chips of the individual semiconductor light-emitting devices 10.

(Screening Step)

Finally, at the screening step S103, with respect to the individualized semiconductor light-emitting devices 10 (chips), semiconductor light-emitting devices 10 other than those not determined as defective as a result of the quality determination of the inspection step S101 are screened as acceptable. Thus, chips having defective light-emitting regions and therefore being highly likely to decrease in luminance or fail due to time deterioration can be removed as defective devices as well as defective devices of low luminance average.

Now concrete examples of the singulation step S102 and the screening step S103 are described in detail below. It is noted that steps from a 'front-surface side adhesive sheet bonding step' to a 'back-surface-side adhesive sheet stretching step' described below correspond to the singulation step S102, and a 'acceptable device extracting step' corresponds to the screening step S103.

(Front-Surface-Side Adhesive Sheet Bonding Step)

After the quality determination as to the individual semiconductor light-emitting devices 10 at the inspection step S101 is finished, an adhesive sheet coated with a UV (Ultraviolet)-curing type adhesive is bonded to the whole top surface (surface on which semiconductor layers are stacked) of the wafer in which semiconductor light-emitting devices 10 are two-dimensionally arrayed. This adhesive sheet is a sheet in which, for example, a resin sheet of polyolefine or the like is coated with an adhesive that is cured and decrease adhesiveness by UV irradiation.

(Dicing Step)

Next, the wafer is subjected to dicing from the back surface side, i.e. growth substrate 11 side, of the wafer, by which the light-emitting devices 10 are divided.

(Back-Surface-Side Adhesive Sheet Stretching Step)

Next, an adhesive sheet is bonded to the back surface side of each semiconductor light-emitting device 10. The adhesive sheet to be bonded on the back surface side may be one similar to the adhesive sheet bonded on the front surface side, but it is preferable that the adhesive sheet has stretchability and that the adhesive is other than the ultraviolet-curing type.

(Front-Surface-Side Adhesive Sheet Peeling Step)

Next, UV light is applied to the front-surface-side adhesive sheet so that the adhesive is cured so as to lose the adhesiveness. Then, the front-surface-side adhesive sheet having lost the adhesive power is peeled off. Thus, it follows that the adhesive sheet is bonded on the back surface side of each semiconductor light-emitting device 10.

(Back-Surface-Side Adhesive Sheet Stretching Step)

Next, the back-surface-side adhesive sheet is stretched in longitudinal-and-lateral array directions of the semiconductor light-emitting devices 10. As a result of this, the semiconductor light-emitting devices 10 singulated in the dicing step can be made apart from one another while keeping their positional relation of two-dimensional array. Thus, the semiconductor light-emitting devices 10 can more easily pick up individually.

(Acceptable Device Extracting Step)

Next, acceptable semiconductor light-emitting devices 10 are extracted according to the total determination result determined on the semiconductor light-emitting device 10 basis at the inspection step S101. The extraction of semiconductor light-emitting devices 10 may be performed by, for example, attaching a collet having a suction nozzle at its end to an XYZ stage, moving the collet to positions where a semiconductor light-emitting device 10 determined as an acceptable device is placed, one after another, and sucking and picking up the semiconductor light-emitting device 10 from the front surface side of the wafer by the collet. In picking up of a semiconductor light-emitting device 10 by the collet, it is preferable that the semiconductor light-emitting device 10 is pushed up by a pin from the back surface side of the wafer via the adhesive sheet. With this arrangement, the semiconductor light-emitting device 10, which is an object of extraction, can be picked up easily from the adhesive sheet.

Although acceptable devices are picked up in this embodiment, it is also allowable that defective devices are picked up and removed. In this case, it follows the semiconductor light-emitting devices 10 that are left after removal of all the defective devices are screened as acceptable.

Although the inspection method for a semiconductor light-emitting device, as well as the semiconductor light-emitting device manufacturing method including the inspection method as a step, according to the present invention have been described specifically by way of embodiments of the invention hereinabove, yet the gist of the invention is not limited to these descriptions and should be widely construed based on the description of appended claims. Also, it is needless to say that changes and modifications of the embodiments in various ways based on those descriptions are included in the gist of the invention.

REFERENCE SIGNS LIST 1 inspection apparatus
2 image capturing unit (image input means)
21 irradiating light source
22 image capturing means
23 dichroic mirror
24 objective lens
25 mount
3 analysis unit
31 inspection region extracting means
32 inspection-region information storage means
33 luminance average determination means (photoluminescence intensity average determination means)
34 luminance variance determination means (photoluminescence intensity variation determination means)
35 total determination means
36 determination result storage means
10 semiconductor light-emitting device (light-emitting device)
11 growth substrate
12 semiconductor multilayered body
12n n-type semiconductor layer
12p p-type semiconductor layer
12a active layer
12b recess portion
13n n-side electrode
13p p-side electrode
13a diffusion electrode
13b extracted portion
14 protective film
15 dividing region
15a reference point
15b borderline
16 light-emitting region
W inspection object

The invention claimed is:

1. A method of inspecting a semiconductor light-emitting device having an active layer, the method comprising:
irradiating the semiconductor light-emitting device with light of a shorter wavelength than light emitted from the active layer, using an irradiating light source;
capturing an image of photoluminescence emitted from the active layer upon the irradiation of the semiconductor light-emitting device, using an image sensor;
extracting a region of the semiconductor light-emitting device from the captured image, as an inspection region, using a computer;
calculating an average value of a photoluminescence intensity over pixels in the inspection region, using the computer;
calculating a variation value indicating a degree of variation of the photoluminescence intensity over the pixels in the inspection region, using the computer; and
determining that the semiconductor light-emitting device is defective upon determining that at least one of (i) the average value of the photoluminescence intensity is smaller than a predetermined first threshold, and (ii) the variation value is larger than a predetermined second threshold, using the computer.

2. The method according to claim 1, wherein
the inspection region is a region other than predetermined non-emitting regions of the semiconductor light-emitting device.

3. The method according to claim 2, wherein
the captured image is a color image composed of color components of red, green and blue, and the photoluminescence intensity is given by using a luminance value which is calculated as a weighted average obtained by providing predetermined weighting to the color components.

4. The method according to claim 3, wherein
the step of capturing an image of photoluminescence emitted from the active layer comprises capturing an image of a plurality of semiconductor light-emitting devices at once, and
wherein the step of extracting a region of the semiconductor light-emitting device comprises separately extracting a region of each of the semiconductor light-emitting devices from the extracted image, as an inspection region.

5. The method according to claim 4, wherein
the variation value is determined based on any one of variance, standard deviation, average deviation and coefficient of variation of photoluminescence intensity in the inspection region.

6. The method according to claim 5, wherein
the average value of the photoluminescence intensity and the variation value are calculated in parallel.

7. The method according to claim 2, wherein
the captured image is a color image composed of color components of red, green and blue, and the photoluminescence intensity is given by using a pixel value of a color component having the highest sensitivity to light of wavelength emitted from the active layer excited by the irradiation light.

8. The method according to claim 7, wherein
the step of capturing an image of photoluminescence emitted from the active layer comprises capturing an image of a plurality of semiconductor light-emitting devices at once, and
wherein the step of extracting a region of the semiconductor light-emitting device comprises separately extracting a region of each of the semiconductor light-emitting devices from the extracted image, as an inspection region.

9. The method according to claim 8, wherein
the variation value is determined based on any one of variance, standard deviation, average deviation and coefficient of variation of photoluminescence intensity in the inspection region.

10. The method according to claim 9, wherein
the average value of the photoluminescence intensity and the variation value are calculated in parallel.

11. The method according to claim 2, wherein
the step of capturing an image of photoluminescence emitted from the active layer comprises capturing an image of a plurality of semiconductor light-emitting devices at once, and
wherein the step of extracting a region of the semiconductor light-emitting device comprises separately extracting a region of each of the semiconductor light-emitting devices from the extracted image, as an inspection region.

12. The method according to claim 2, wherein
the variation value is determined based on any one of variance, standard deviation, average deviation and coefficient of variation of photoluminescence intensity in the inspection region.

13. A method for manufacturing a semiconductor light-emitting device, the method comprising:
forming a semiconductor light-emitting device;
inspecting the semiconductor light-emitting device formed in the step of forming the semiconductor light-emitting device to determine whether or not the semiconductor light-emitting device is defective; and
determining that the semiconductor light-emitting device is an acceptable device when the semiconductor light-emitting device is not determined as defective in the step of inspecting the semiconductor light-emitting device,
wherein the step of inspecting the semiconductor light-emitting device is implemented according to the inspection method defined in claim 2.

14. The method according to claim 1, wherein
the captured image is a color image composed of color components of red, green and blue, and the photoluminescence intensity is given by using a luminance value which is calculated as a weighted average obtained by providing predetermined weighting to the color components.

15. The method according to claim 1, wherein
the captured image is a color image composed of color components of red, green and blue, and the photoluminescence intensity is given by using a pixel value of a color component having the highest sensitivity to light of wavelength emitted from the active layer excited by the irradiation light.

16. The method according to claim 1, wherein
the step of capturing an image of photoluminescence emitted from the active layer comprises capturing an image of a plurality of semiconductor light-emitting devices at once, and
wherein the step of extracting a region of the semiconductor light-emitting device comprises separately extracting a region of each of the semiconductor light-emitting devices from the extracted image, as an inspection region.

17. The method for according to claim 1, wherein
the variation value is determined based on any one of variance, standard deviation, average deviation and coefficient of variation of photoluminescence intensity in the inspection region.

18. The method according to claim 1, wherein
the average value of the photoluminescence intensity and the variation value are calculated in parallel.

19. A method of manufacturing a semiconductor light-emitting device, the method comprising:
forming a semiconductor light-emitting device;
inspecting the semiconductor light-emitting device formed in the step of forming the semiconductor light-emitting device to determine whether or not the semiconductor light-emitting device is defective; and
determining that the semiconductor light-emitting device is an acceptable device when the semiconductor light-emitting device is not determined as defective in the step of inspecting the semiconductor light-emitting device,
wherein the step of inspecting the semiconductor light-emitting device is implemented according to the inspection method defined in claim 18.

20. A method of manufacturing a semiconductor light-emitting device, the method comprising:
forming a semiconductor light-emitting device;
inspecting the semiconductor light-emitting device formed in the step of forming the semiconductor light-emitting device to determine whether or not the semiconductor light-emitting device is defective; and
determining that the semiconductor light-emitting device is an acceptable device when the semiconductor light-emitting device is not determined as defective in the step of inspecting the semiconductor light-emitting device,
wherein the step of inspecting the semiconductor light-emitting device is implemented according to the inspection method defined in claim 1.

* * * * *